United States Patent
Ye et al.

(10) Patent No.: US 10,373,350 B2
(45) Date of Patent: Aug. 6, 2019

(54) APPARATUS AND METHOD FOR CT DATA RECONSTRUCTION BASED ON MOTION COMPENSATION

(71) Applicants: VATECH Co., Ltd., Gyeonggi-do (KR); VATECH EWOO Holdings Co., Ltd., Gyeonggi-do (KR); Korea Advanced Institute of Science and Technology, Daejeon (KR)

(72) Inventors: Jong chul Ye, Daejeon (KR); Ja wook Gu, Daejeon (KR); Tae Woo Kim, Gyeonggi-do (KR); Sung Il Choi, Gyeonggi-do (KR); Woong Bae, Gyeonggi-do (KR)

(73) Assignees: VATECH Co., Ltd., Gyeonggi-do (KR); VATECH EWOO Holdings Co., Ltd., Gyeonggi-do (KR); Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/654,868

(22) Filed: Jul. 20, 2017

(65) Prior Publication Data
US 2018/0025511 A1 Jan. 25, 2018

(30) Foreign Application Priority Data

Jul. 22, 2016 (KR) .................. 10-2016-0093759
Dec. 16, 2016 (KR) .................. 10-2016-0172635

(51) Int. Cl.
*G06T 11/00* (2006.01)
*A61B 6/00* (2006.01)
*G06T 7/285* (2017.01)
*A61B 6/03* (2006.01)
*A61B 6/14* (2006.01)

(52) U.S. Cl.
CPC .......... *G06T 11/006* (2013.01); *A61B 6/5205* (2013.01); *A61B 6/5264* (2013.01); *G06T 7/285* (2017.01); *G06T 11/005* (2013.01); *A61B 6/032* (2013.01); *A61B 6/14* (2013.01); *G06T 2207/10081* (2013.01); *G06T 2211/412* (2013.01)

(58) Field of Classification Search
CPC ..... A61B 6/032; A61B 6/5264; A61B 5/7207; A61B 8/5276; A61B 6/5205; G06T 2207/10081; G06T 7/20; G06T 11/006; G06T 7/285; G06T 11/005
See application file for complete search history.

(56) References Cited

U.S. PATENT DOCUMENTS

2007/0177713 A1* 8/2007 Kohler .................. G06T 11/005
378/4
2011/0293155 A1* 12/2011 Nakanishi ............. G06T 11/005
382/131

* cited by examiner

*Primary Examiner* — Kenny A Cese
(74) *Attorney, Agent, or Firm* — IP Legal Services, LLC

(57) ABSTRACT

Disclosed is an apparatus for computed tomography (CT) image data reconstruction based on motion compensation. The apparatus for computed tomography (CT) data reconstruction based on motion compensation, the apparatus including a storage configured to store projection radiographs and an image processor configured to obtain pairs of opposite projection radiographs from the projection radiographs, and compensate a movement of a radiography subject based on a correlation between the projection radiographs of each pair of opposite projection radiographs.

9 Claims, 9 Drawing Sheets

APPARATUS AND METHOD FOR CT DATA RECONSTRUCTION BASED ON MOTION COMPENSATION

CROSS REFERENCE TO RELATED APPLICATION

The present application claims priority to Korean Patent Application Nos. 10-2016-0093759 and 10-2016-0172635, respectively field on Jul. 22, 2016 and Dec. 16, 2016, the entire contents of which are incorporated herein for all purposes by this reference.

BACKGROUND OF THE INVENTION

Field of the Invention

The present invention relates generally to a technology for computed tomography (CT) data reconstruction. More particularly, the present invention relates to CT data reconstruction based on motion compensation.

Description of the Related Art

Computed Tomography (hereinafter, designated as CT) is known as a medical image processing method that provides a three-dimensional radiograph for a radiography subject by performing X-ray radiography on the radiography subject at different angles. A three-dimensional medical radiograph obtained using CT is widely used in treatment and medical fields because an inner section, etc. of the radiography subject are precisely shown in detail in a non-destructive manner. A CT apparatus includes a CT gantry having an X-ray source and X-ray detector arranged to each other across a radiography subject. In order to obtain a CT radiograph, the CT gantry rotates on a fixed axis between the X-ray source and the X-ray detector while the radiography subject is irradiated with an X-ray beam by the X-ray source. The X-ray beam passed through the radiography subject is detected by the X-ray detector, and projection data of the radiography subject is obtained in different directions and is used to reconstruct CT data.

However, as described above, during obtaining of the projection data of the radiography subject from different directions, even when a patient who is the radiography subject slightly moves, the quality of the CT radiograph may not be ensured due to a motion artifact effect. Immobilization tools may be used to restrain the radiography subject from moving, but there are limits in preventing the radiography subject from moving by immobilization tools. Also, a sensor such as a camera, etc. may be used to sense motion of the radiography subject, and there is a method of correcting the projection data at a time when motion is sensed in inverse of the motion. However, in this case, a sensor for sensing motion of the radiography subject is required and excessive time and computation to compare different information is necessary, sensed result of the sensor and projection data.

Thus, a method for CT data reconstruction that can provide a CT radiograph with reliable quality even though a patient moves without immobilization tools and sensors is required in this technical field.

The foregoing is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problems occurring in the related art, and the present invention is intended to propose an apparatus and method for CT data reconstruction that can provide a CT radiograph with reliable quality even though a radiography subject moves using only projection data without immobilization tools and sensors.

It is to be understood that technical problems to be solved by the present disclosure are not limited to the aforementioned technical problems and other technical problems which are not mentioned will be apparent from the following description to a person with an ordinary skill in the art to which the present disclosure pertains.

In order to achieve the above object, according to one aspect of the present invention, there is provided an apparatus for computed tomography (CT) data reconstruction based on motion compensation, the apparatus including: a storage configured to store N CT projection radiographs, wherein N is a natural number; and an image processor configured to obtain pairs of opposite projection radiographs from the N CT projection radiographs, and to determine whether or not a radiography subject has moved based on a correlation between the projection radiographs of each pair of opposite projection radiographs.

In an embodiment, the image processor may be configured such that when determining the radiography subject has moved, the image processor performs the motion compensation on one projection radiograph of each of the N/2 pairs of opposite projection radiographs so as to generate motion-compensated projection radiographs, and reconstructs CT data by using motion-uncompensated CT projection radiographs and the motion-compensated projection radiographs of the N CT projection radiographs.

In an embodiment, each of the N/2 pairs of opposite projection radiographs may include a first projection radiograph and a second projection radiograph, and for each of the N/2 pairs of opposite projection radiographs, the image processor may be further configured to determine both a first motion vector for the second projection radiograph based on the first projection radiograph and a second motion vector for the first projection radiograph based on the second projection radiograph.

In an embodiment, the image processor may be further configured to perform smoothing filtering on determined N/2 first motion vectors, and to perform the smoothing filtering on determined N/2 second motion vectors.

In an embodiment, wherein for each of the N/2 pairs of opposite projection radiographs, the image processor may be further configured to (i) perform the motion compensation on the second projection radiograph using the first motion vector so as to generate motion-compensated second projection radiographs, (ii) reconstruct a first sectional image from the motion-compensated second projection radiograph and remaining CT projection radiographs except for second projection radiographs of the N CT projection radiographs, (iii) perform the motion compensation on the first projection radiograph using the second motion vector so as to generate motion-compensated first projection radiographs, (iv) reconstruct a second sectional image using the motion-compensated first projection radiographs and remaining CT projection radiographs except for first projection radiographs of the N CT projection radiographs, (v) identify which image of the first sectional image and the second sectional image has higher resolution, and (vi) determine the motion-compensated second projection radiograph as the motion-compensated projection radiograph when identifying resolution of the first sectional image is higher than resolution of the second sectional image, or determine the motion-compensated first projection radiographs as the motion-compensated projection radiographs when identifying the resolution of the second sectional image is higher than the resolution of the first sectional image.

In an embodiment, wherein for each of the N/2 pairs of opposite projection radiographs, the image processor may be further configured to (i) set a first patch in the first projection radiograph, (ii) set a first search area in the second projection radiograph, wherein the first search area includes an area corresponding to the first patch, (iii) determine a location where similarity between the first patch and a second patch is highest as a location of the second patch while in the first search area, moving the second patch corresponding to the first patch, (iv) determine the first motion vector based on a location of the first patch and the location of the second patch, (v) set a third patch in the second projection radiograph, (vi) set a second search area in the first projection radiograph, wherein the second search area surrounds an area corresponding to the third patch, (vii) determine a location where similarity between the third patch and a fourth patch is highest as a location of the fourth patch while in the second search area, moving the fourth patch corresponding to the third patch, and (viii) determine the second motion vector based on a location of the third patch and the location of the fourth patch.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

The above and other aspects, features, and advantages of the present invention will become apparent from the detailed description of the following embodiments in conjunction with the accompanying drawings. It should be understood that the present invention is not limited to the following embodiments and may be embodied in different ways, and that the embodiments are given to provide complete disclosure of the invention and to provide a thorough understanding of the present invention to those skilled in the art. The scope of the present invention is defined only by the claims.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

In the embodiment of the present invention, terms such as 'module' or 'unit' indicate a unit for performing at least one function or operation, and may be implemented by hardware or software, or a combination of both. Also, a plurality of "modules" or a plurality of "units" may be integrated as at least one module and thus implemented with at least one processor, except for "module" or "unit" that is implemented with specific hardware.

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification and the relevant art and will not be interpreted in an idealized or overly formal sense unless expressly so defined herein.

Hereinafter, embodiments of the present invention will be described in detail with reference to the accompanying drawings. However, in the following description, it should be noted that, when the functions of conventional elements and the detailed description of elements related with the present invention may make the gist of the present invention unclear, a detailed description of those elements will be omitted.

Figure 1:
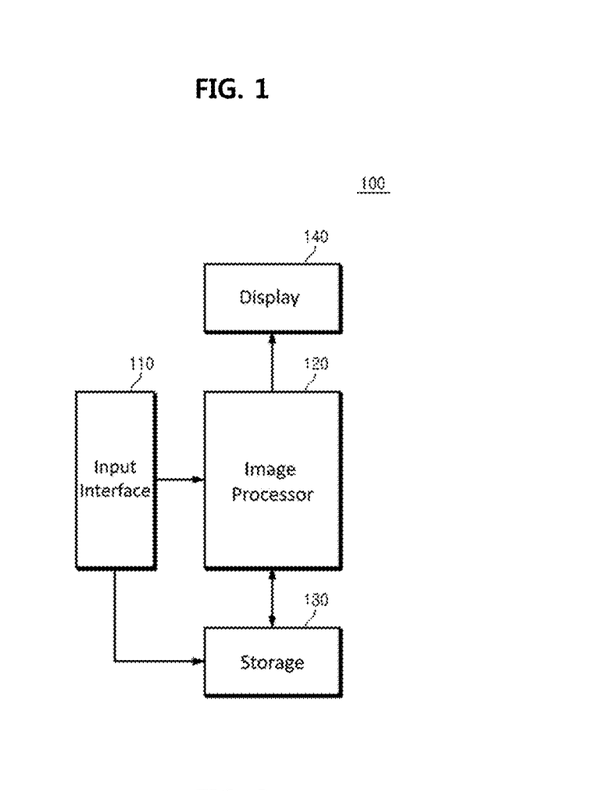
FIG. 1 is a view illustrating configuration of an apparatus for CT data reconstruction based on motion compensation according to an embodiment of the present invention.

FIG. 1 is a view illustrating configuration of an apparatus for CT data reconstruction based on motion compensation according to an embodiment of the present invention.

As shown in FIG. 1, according to the embodiment of the present invention, the apparatus 100 for CT data reconstruction may include an input interface 110, an image processor 120, a storage 130, and a display 140. The input interface 110 may be used for inputting projection data indicating CT projection radiographs in a frame unit, which are obtained by a CT apparatus (not shown) such as a cone beam CT apparatus, to the storage 130. The projection data is projection data of a radiography subject obtained in different directions by performing X-ray radiography using a CT apparatus. The CT apparatus includes a gantry having an X-ray source and an X-ray detector arranged to face each other across the radiography subject. The CT apparatus is operated by rotating the gantry on a rotation axis that is an axis between the X-ray source and the X-ray detector. Here, the rotation axis may be fixed in a longitudinal direction of the radiography subject.

Figure 2:
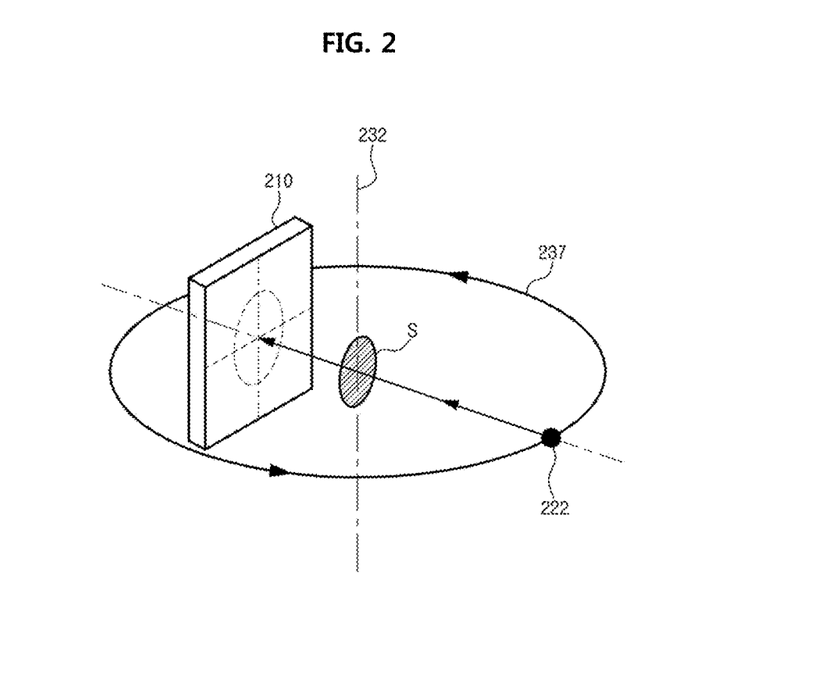
FIG. 2 is a view illustrating a principle of obtaining projection data where a radiography subject is irradiated with an X-ray beam by an X-ray source, and an X-ray detector detects the X-ray beam having passed through the subject.

As shown in FIG. 2, the CT gantry (not shown) of the CT apparatus having the X-ray source 222 rotates along a trajectory 237 on the fixed rotation axis 232 passing through the radiography subject S. The radiography subject S is irradiated with an X-ray beam by the X-ray source 222 and the X-ray beam having passed through the radiography subject S is detected by the X-ray detector 210. Here, multiple pieces of data in a frame unit obtained by detecting the X-ray beam from the X-ray source 222 rotating with the CT gantry by the X-ray detector 210 are called projection data. Multiple pieces of projection data in a frame unit detected by the X-ray detector 210 may include information on multiple CT projection radiographs. The input interface 110 may be composed of hardware and software modules for inputting a user command to perform radiograph analysis/processing according to the embodiments of the present invention. The input interface 110 may be used in inputting necessary various commands to the image processor 120, or in indicating a part of or whole radiograph on the display 140 to perform various types of radiograph processing thereon. In the embodiment, the input interface 110 may include a keyboard of a computer, a keypad, a touchpad, a mouse, etc., but types of the input interface are not limited thereto. For example, the input interface 110 may include the graphic user interface that can be controlled using the above-described input devices. The display 140 displays a three-dimensional CT radiograph or sectional images thereof or both that are reconstructed according to the embodiments of the present invention. The display 140 may include various display devices such as an LCD, an LED display, an AMOLED display, a CRT display, etc.

Figure 3:
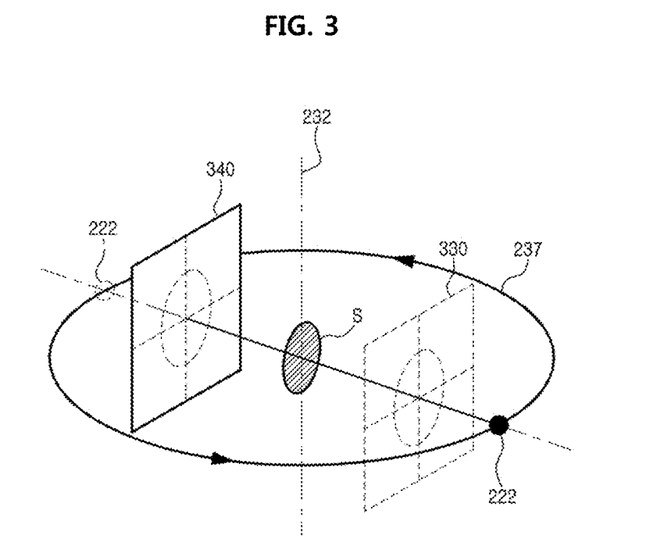
FIG. 3 is a view illustrating an example of a pair of opposite projection radiographs according to an embodiment of the present invention in a case where a radiography subject does not move during CT radiography.

The storage 130 may be used for storing the projection data indicating CT projection radiographs. The image processor 120 may obtain multiple pairs of opposite projection radiographs 330 and 340 from the CT projection radiographs stored in the storage 130. As shown in FIG. 3, a pair of opposite projection radiographs 330 and 340 is two radiographs in which the locations of the X-ray detector 210 at the time when the two radiographs are obtained differ from each other by 180°. In FIG. 3, for convenience of explanation, a CT projection radiograph frame which is projection data detected by the X-ray detector 210 is illustrated at the location of the X-ray detector 210. Also, hereinafter, for convenience of explanation, the projection radiograph frame(s) is called 'projection radiograph(s)'. For example, the pair of opposite projection radiographs 330 and 340 may be composed of a projection radiograph obtained when the X-ray detector 210 is located at 0° and a projection radiograph obtained when the X-ray detector 210 is located at 180°. As another example, the pair of opposite projection radiographs 330 and 340 may be composed of a projection radiograph obtained when the X-ray detector 210 is located at 30° and a projection radiograph obtained when the X-ray detector 210 is located at 210°. When the total number of CT projection radiographs is N, the number of a pair 330 of opposite projection radiographs may be N/2. The storage 130 may be used in storing: radiograph data (for example, data of motion-compensated radiographs) which is an intermediate result of performing radiograph processing according to the embodiments of the present invention; another radiograph data (for example, reconstructed CT data or sectional image data thereof or both) which is a final result of performing radiograph processing according to the embodiments of the present invention; and variable values (for example, motion vectors) that are necessary to perform radiograph processing according to the embodiment of the present invention. The storage 130 may further store software/firmware, etc. that are required to implement the image processor 120. The storage 130 may be implemented as any one storage medium of a flash memory, a hard disk, MultiMedia Card (MMC), a card-type memory (e.g., Secure Digital (SD) card or eXtream Digital (XD) card, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but it is obvious to an ordinary skilled person in the art that it is not limited thereto.

The image processor 120 may perform predetermined radiograph processing such as pre-processing filtering, etc. for CT projection radiographs. Hereinbelow, both CT projection radiographs or CT projection radiographs on which radiograph processing is performed are called 'CT projection radiographs' or 'projection radiographs'.

Figure 4:
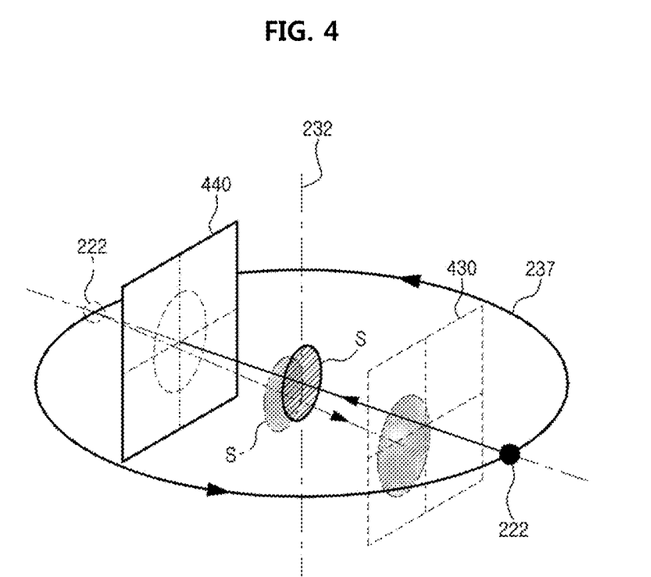
FIG. 4 is a view illustrating an example of a pair of opposite projection radiographs according to an embodiment of the present invention in a case where a radiography subject moves during CT radiography.

When the total number of CT projection radiographs is N, the image processor 120 may perform motion compensation on one projection radiograph of each of N/2 pairs of opposite projection radiographs 330 and 340 so as to generate motion-compensated projection radiographs. During radiography using the CT apparatus, when a patient who is a radiography subject S does not move, a correlation between the projection radiograph 330 obtained at a location and the projection radiograph 340 obtained at the opposite location, namely, rotated therefrom by 180° may be maximum as shown in FIG. 3. That is, in this case, the pair of opposite projection radiographs 330 and 340 may be radiographs having the maximum correlation therebetween. However, as shown in FIG. 4, during radiography using the CT apparatus, when the radiography subject S moves, a projection radiograph 430 obtained when the radiography subject S moves has a low correlation with a projection radiograph 440 obtained at the opposite location, namely, rotated therefrom by 180°.

Accordingly, the image processor 120 may obtain multiple pairs of opposite projection radiographs 430 and 440 from CT projection radiographs stored in the storage 130, and may sense or determine whether or not the radiography subject has moved based on a correlation between each pair of projection radiographs.

When motion of the radiography subject S is a translating rigid motion, the projection radiograph 430 obtained when the radiography subject S moves may be compensated by estimating motion based on the opposite projection radiograph 440. Likewise, even though a projection radiograph obtained when the radiography subject S moves is the projection radiograph 440, the projection radiograph 440 may be compensated by estimating motion based on the opposite projection radiograph 430. Hereinbelow, the projection radiographs 430 and 440 composing the pair of opposite projection radiographs are called a 'first projection radiograph 430' and a 'second projection radiograph 440'.

For each of N/2 pairs of opposite projection radiographs 430 and 440, the image processor 120 may determine a first motion vector for the second projection radiograph 440 based on the first projection radiograph 430 and a second motion vector for the first projection radiograph 430 based on the second projection radiograph 440. In the embodiment, the image processor 120 may determine the first motion vector and the second motion vector using a patch matching algorithm or a block matching algorithm. The image processor 120 may perform smoothing filtering on the determined N/2 first motion vectors, and may perform smoothing filtering on the determined N/2 second motion vectors.

For each of N/2 pairs of opposite projection radiographs 430 and 440, the image processor 120 may select one of a motion-compensated second projection radiograph generated by compensating the second projection radiograph 440 using the first motion vector and a motion-compensated first projection radiograph obtained by compensating the first projection radiograph 430 using the second motion vector, as an intended motion-compensated projection radiograph. In the embodiment, the selection may be based on resolution difference between a result of CT data reconstruction using the motion-compensated second projection radiographs and remaining CT projection radiographs except for the second projection radiographs 440 of the N CT projection radiographs and a result of CT data reconstruction using the motion-compensated first projection radiographs and remaining CT projection radiographs except for the first projection radiographs 430 of the N CT projection radiographs. When the result of CT radiograph reconstruction using the motion-compensated second projection radiographs is better than the result of CT radiograph reconstruction using the motion-compensated first projection radiographs, it is estimated that the second projection radiograph 440 was obtained when the radiography subject S moved. Thus, it is reasonable to use the motion-compensated second projection radiograph among the pair of opposite projection radiographs 430 and 440 for the final CT reconstruction.

Instead of using N CT projection radiographs for CT radiograph reconstruction as in a conventional technology, the image processor 120 may reconstruct CT data using N/2 CT projection radiographs on which motion compensation is not performed and N/2 projection radiographs on which motion compensation is performed among N CT projection radiographs. Accordingly, it is possible to significantly enhance the definition of a three-dimensional radiograph or sectional images thereof being rendered based on CT data reconstructed using the motion-compensated projection radiographs. Reconstruction of CT data may be performing using a CT reconstruction algorithm such as a well known 'back projection algorithm'. The back projection algorithm is that multi-directional X-ray projection data is projected onto each position in the radiography subject to obtain relative X-ray attenuation at the location. The back projection algorithm is well known in this technical field, thus detailed description thereof will be omitted. For reference, the CT reconstruction algorithm that can be applied to the embodiment of the present invention is not limited to the above-described algorithm.

Figure 5:
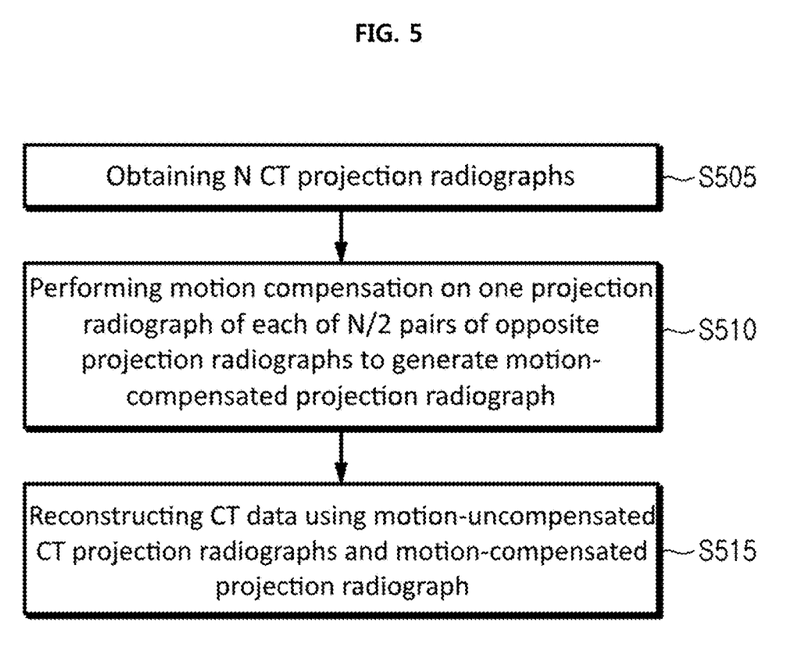
FIG. 5 is a flowchart illustrating a method for CT data reconstruction based on motion compensation according to an embodiment of the present invention.

FIG. 5 is a flowchart illustrating a method for CT data reconstruction based on motion compensation according to an embodiment of the present invention.

Figure 6:
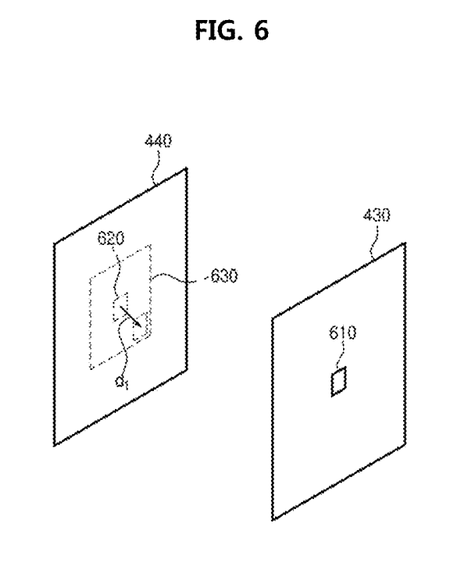
FIG. 6 is a view illustrating a way of determining a first motion vector according to an embodiment of the present invention.
Figure 7:
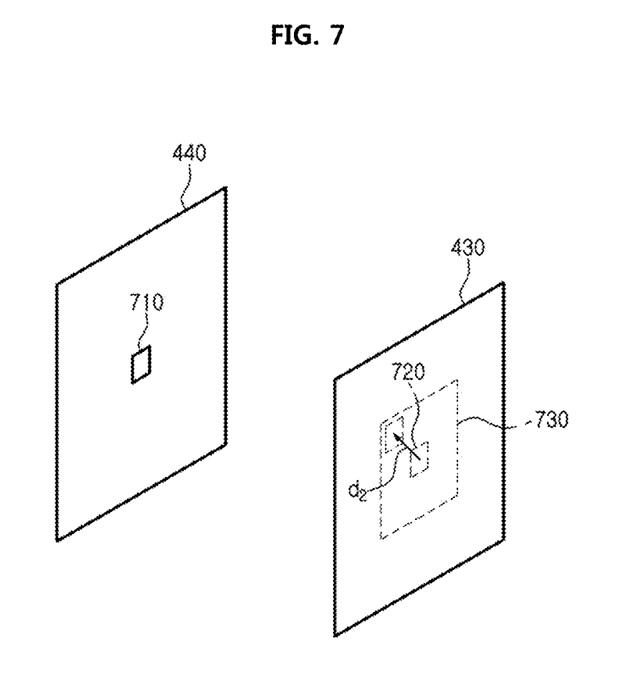
FIG. 7 is a view illustrating a way of determining a second motion vector according to an embodiment of the present invention.

The method for CT data reconstruction according to the embodiment of the present invention starts with obtaining N CT projection radiographs at step S505. The N CT projection radiographs may be obtained by storing projection data detected by the X-ray detector 210 N times in the storage 130. As described above, N/2 pairs of opposite projection radiographs 430 and 440 composed of the first projection radiograph 430 and the second projection radiograph 440 may be the N projection radiographs. Motion compensation is performed on one projection radiograph of each of N/2 pairs of opposite projection radiographs 430 and 440 to generate a motion-compensated projection radiograph at step S510. At this step, as shown in FIGS. 6 and 7, for each of N/2 pairs of opposite projection radiographs 430 and 440, it is possible to determine a first motion vector $d_1$ for the second projection radiograph 440 based on the first projection radiograph 430 and a second motion vector $d_2$ for the first projection radiograph 430 based on the second projection radiograph 440.

Hereinafter, a process of determining the first motion vector $d_1$ and the second motion vector $d_2$ will be disclosed with reference to FIGS. 6 to 8. Steps described below may be performed on each of N/2 pairs of opposite projection radiographs 430 and 440.

Figure 8:
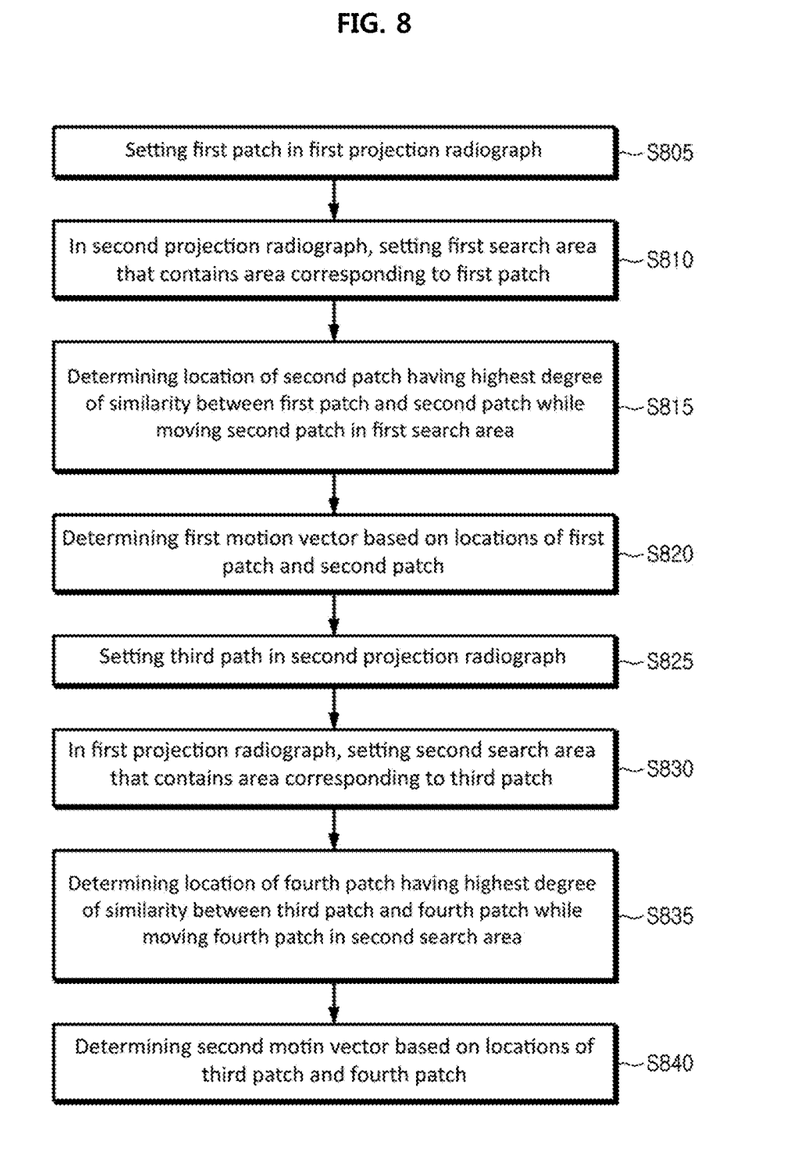
FIG. 8 is a flowchart illustrating a process of determining a first motion vector and a second motion vector according to an embodiment of the present invention.

Referring to FIG. 8, the process starts with setting a first patch 610 in the first projection radiograph 430 at step S805. In the embodiment, the first patch 610 may be set as a small block at the central portion of the first projection radiograph 430. In another embodiment, the first patch 610 may be set as a small block at a portion having a feature of the first projection radiograph 430. A first search area 630 containing an area corresponding to the first patch 610 is set in the second projection radiograph 440 at step S810. The size of the first search area 630 is sufficiently larger than the size of the first patch 610, and is smaller than the size of the second projection radiograph 440 so as not to excessively increase a computation load of the image processor 120. While moving a second patch 620 corresponding to the first patch 610 in the first search area 630, a location where similarity between the first patch 610 and the second patch 620 is the highest is determined as a location of the second patch 620 at step S815. Here, one of correlation and mean square error (MSE) may be selected as a measure indicating similarity. The first motion vector $d_1$ is determined based on the locations of the first patch 610 and the second patch 620 at step S820. When the second projection radiograph 440 is placed on an XY plane indicating coordinates (x, y), for example, the first patch 610 has reference coordinates (300, 400) and the second patch 620 has reference coordinates (302, 405), the first motion vector $d_1$ may be coordinates (2, 5).

A third patch 710 is set in the second projection radiograph 440 at the step S825. In the embodiment, the third patch 710 may be set as a small block at the central portion of the second projection radiograph 440. In another embodiment, the third patch 710 may be set as a small block at a portion having a feature of the second projection radiograph 440. A second search area 730 containing an area corresponding to the third patch 710 is set in the first projection radiograph 430 at step S830. The size of the second search area 730 is sufficiently larger than the size of the third patch 710, and is smaller than the size of the first projection radiograph 430 so as not to excessively increase a computation load of the image processor 120. While moving a fourth patch 720 corresponding to the third patch 710 in the second search area 730, a location where similarity between the third patch 710 and the fourth patch 720 is the highest is determined as a location of the fourth patch 720 at step S835. The second motion vector $d_2$ is determined based on locations of the third patch 710 and the fourth patch 720 at step S840. For example, when the third patch 710 has reference coordinates (302, 405) and the fourth patch 720 has reference coordinates (300, 400), the second motion vector $d_2$ may have coordinates (−2, −5).

Figure 9:
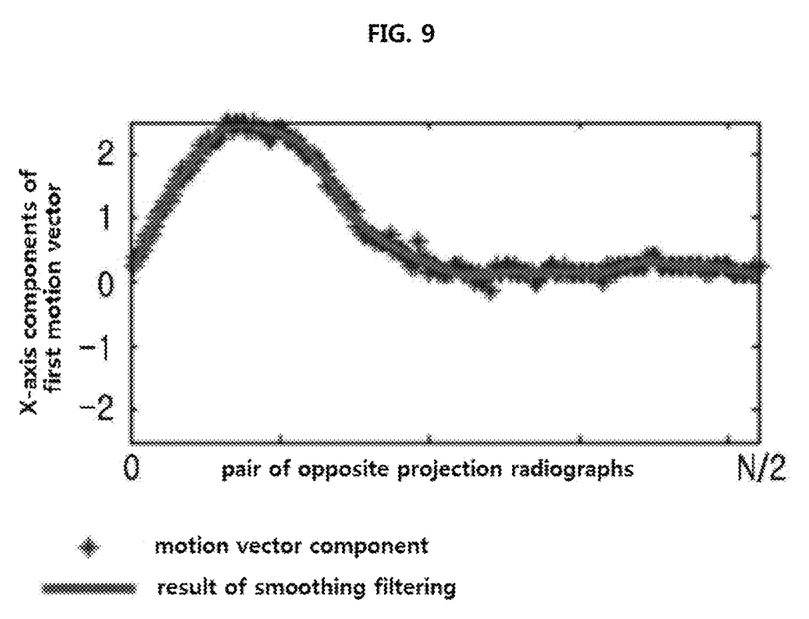
FIG. 9 is a view illustrating X-axis components of N/2 first motion vectors and a simulation result of performing smoothing filtering thereon.

Referring to FIG. 5, smoothing filtering is performed on the first motion vector $d_1$ and the second motion vector $d_2$ that are determined for each of N/2 pairs of opposite projection radiographs 430 and 440 at step S510. When the radiography subject S slowly moves, a value of a motion vector does not rapidly change. Thus, smoothing filtering on a motion vector having abrupt change in a particular projection radiograph is performed using motion vectors for projection radiographs neighboring the particular projection radiograph. In the embodiment, smoothing filtering may be individually performed on N/2 first motion vectors and N/2 second motion vectors. In the embodiment, smoothing filtering may be performed on each component of the motion vector. FIG. 9 is a view illustrating X-axis components of N/2 first motion vectors $d_1$ and a simulation result of performing smoothing filtering thereon. It can be showed in a same way for Y-axis components of N/2 first motion vectors $d_1$ and a simulation result of performing smoothing filtering thereon. Referring to FIG. 9, smoothing filtering is performed on components of wrongly estimated motion vectors.

For each of N/2 pairs of opposite projection radiographs 430 and 440, one projection radiograph is selected from the pair of opposite projection radiographs 430 and 440 for motion compensation, and motion compensation is performed on the selected projection radiograph at step S510. Motion compensation may be performed on the projection radiograph by moving the projection radiograph in a horizontal direction or a vertical direction or both according to the motion vector. In the embodiment, the selection of one projection radiograph may be based on a resolution difference between a result of CT data reconstruction using the motion-compensated second projection radiographs and remaining CT projection radiographs except for the second projection radiographs 440 of the N CT projection radiographs and a result of CT data reconstruction using the motion-compensated first projection radiographs and remaining CT projection radiographs except for the first projection radiographs 430 of the N CT projection radiographs. That is, when the result of CT radiograph reconstruction using the motion-compensated second projection radiographs is better than the result of CT radiograph reconstruction using the motion-compensated first projection radiographs, the motion-compensated second projection radiographs are selected for the final CT data reconstruction.

Hereinbelow, a process of selecting one projection radiograph from a pair of opposite projection radiographs 430 and 440 to perform motion compensation on the selected projection radiograph will be described with reference to FIG. 10. Hereinbelow, steps may be performed on each of N/2 pairs of opposite projection radiographs 430 and 440.

Figure 10:
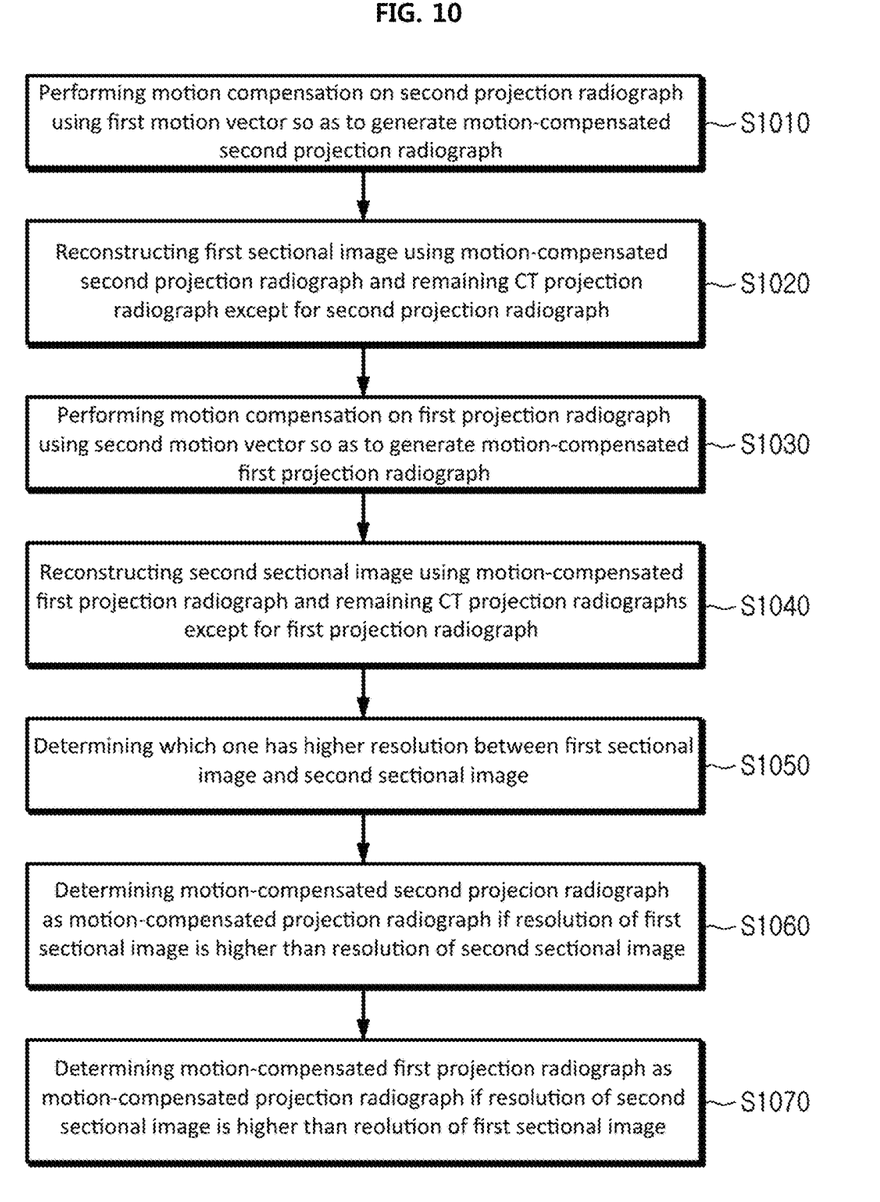
FIG. 10 is a flowchart illustrating a process of selecting one projection radiograph from a pair of opposite projection radiographs to perform motion compensation according to an embodiment of the present invention.

Referring to FIG. 10, the process starts with generating the motion-compensated second projection radiograph by performing motion compensation on the second projection radiograph 440 using the first motion vector $d_1$ at step S1010. A first sectional image is reconstructed using motion-compensated second projection radiograph and remaining CT projection radiographs except for the second projection radiograph 440 of the N CT projection radiographs at step S1020. The motion-compensated first projection radiograph is generated by performing motion compensation on the first projection radiograph 430 using the second motion vector $d_2$ at step S1030. A second sectional image is reconstructed using the motion-compensated first projection radiograph and remaining CT projection radiographs except for the first projection radiograph 430 of the N CT projection radiographs at step S1040. Determining which one has a higher resolution between the first sectional image and the second sectional image is performed at step S1050. If resolution of the first sectional image is higher than that of the second sectional image, the motion-compensated second projection radiograph is determined as the motion-compensated projection radiograph at step S1060. In contrast, if resolution of the second sectional image is higher than that of the first sectional image, the motion-compensated first projection radiograph is determined as the motion-compensated projection radiograph at step S1070.

Referring to FIG. 5, CT data is reconstructed using N/2 CT projection radiographs on which motion compensation is not performed and N/2 projection radiographs on which motion compensation is performed at step S515. As described above, it is possible to significantly enhance the definition of a three-dimensional radiograph or sectional images thereof being rendered based on CT data reconstructed using the motion-compensated projection radiographs. In the embodiment, CT data may be reconstructed using the back projection algorithm.

Figure 11:
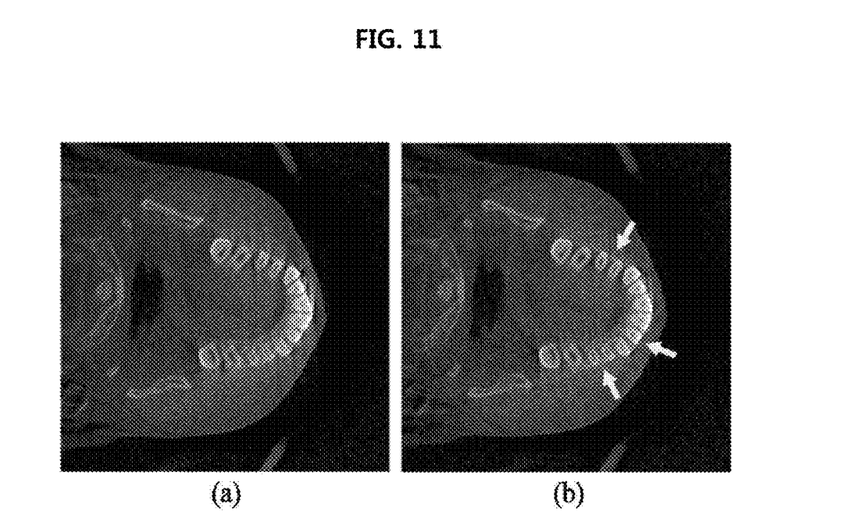
FIGS. 11 to 13 are views respectively illustrating sectional images being rendered by reconstructing CT data according to a conventional technology and sectional images being rendered by reconstructing CT data according to an embodiment of the present invention.
Figure 12:
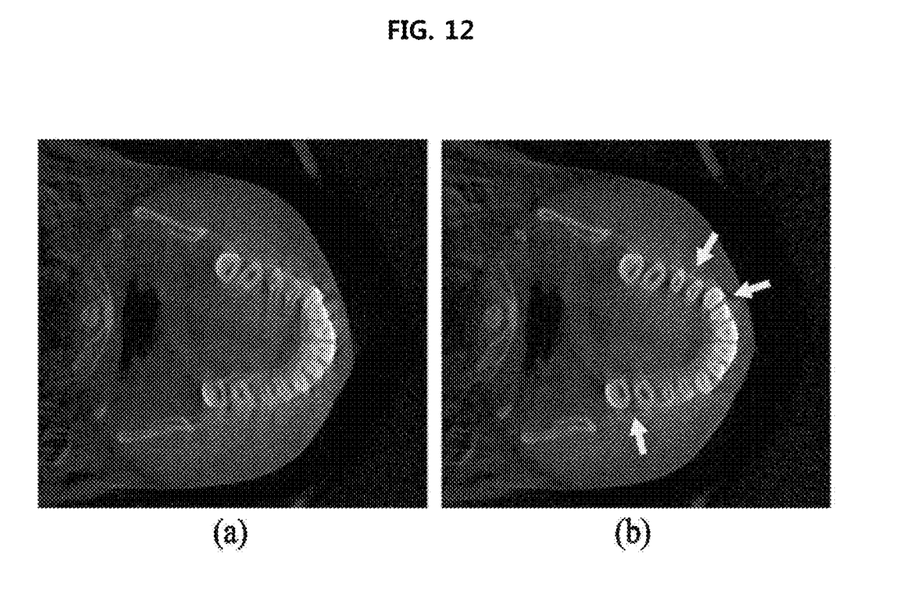
Figure 13:
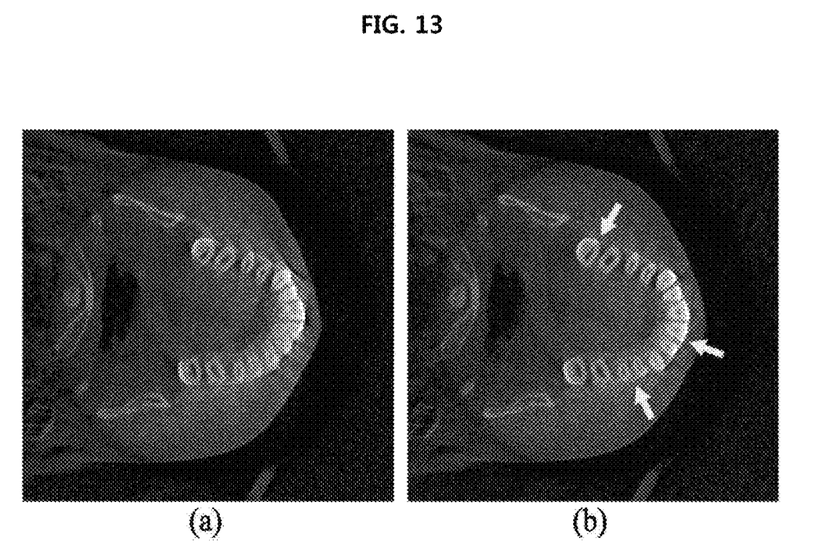

FIGS. 11 to 13 are views respectively illustrating sectional images being rendered by reconstructing CT data according to a conventional technology and sectional images being rendered by reconstructing CT data according to an embodiment of the present invention. FIGS. 11 to 13 (referring to portions marked with arrows) show that resolution of a sectional image being rendered by reconstructing CT data according to the embodiment of the present invention is significantly enhanced, compared to resolution of a sectional image according to a conventional technology.

In the described embodiments of the present invention, arrangement of the described components may vary depending on the environment or requirements to be implemented. For example, some components may be omitted, or several components may be integrated to be operated as one component. In addition, sequence of arrangement of and connection between some components may be changed.

While various embodiments of the present invention have been shown and described, the present invention is not limited to the aforementioned particular embodiments, various modifications are possible by those skilled in the art without departing from the sprit and scope of the accompanying claims, and these modifications should not be understood separately from the scope and spirit. Accordingly, the technical scope of the present invention should be defined only by the accompanying claims.

What is claimed is:

1. An apparatus for computed tomography (CT) data reconstruction based on motion compensation, the apparatus comprising:

a storage configured to store N CT projection radiographs, wherein N is a total number of the stored CT projection radiographs, which is equal to or greater than 2; and an image processor configured to obtain pairs of opposite projection radiographs from the N CT projection radiographs, and to determine whether or not a radiography subject has moved based on a correlation between the projection radiographs of each pair of opposite projection radiographs, wherein each of the N/2 pairs of opposite projection radiographs includes a first projection radiograph and a second projection radiograph, and for each of the N/2 pairs of opposite projection radiographs, the image processor is further configured to determine both a first motion vector for the second projection radiograph based on the first projection radiograph and a second motion vector for the first projection radiograph based on the second projection radiograph, and wherein for each of the N/2 pairs of opposite projection radiographs, the image processor is further configured to (i) perform the motion compensation on the second projection radiograph using the first motion vector so as to generate motion-compensated second projection radiographs, (ii) reconstruct a first sectional image from the motion-compensated second projection radiograph and remaining CT projection radiographs except for second projection radiographs of the N CT projection radiographs, (iii) perform the motion compensation on the first projection radiograph using the second motion vector so as to generate motion-compensated first projection radiographs, (iv) reconstruct a second sectional image using the motion-compensated first projection radiographs and remaining CT projection radiographs except for first projection radiographs of the N CT projection radiographs, (v) identify which image of the first sectional image and the second sectional image has higher resolution, and (vi) determine the motion-compensated second projection radiograph as the motion-compensated projection radiograph when identifying resolution of the first sectional image is higher than resolution of the second sectional image, or determine the motion-compensated first projection radiographs as the motion-compensated projection radiographs when identifying the resolution of the second sectional image is higher than the resolution of the first sectional image.

2. The apparatus of claim 1, wherein for each of the N/2 pairs of opposite projection radiographs, the image processor is further configured to (i) set a first patch in the first projection radiograph, (ii) set a first search area in the second projection radiograph, wherein the first search area includes an area corresponding to the first patch, (iii) determine a location where similarity between the first patch and a second patch is highest as a location of the second patch while in the first search area, moving the second patch corresponding to the first patch, (iv) determine the first motion vector based on a location of the first patch and the location of the second patch, (v) set a third patch in the second projection radiograph, (vi) set a second search area in the first projection radiograph, wherein the second search area surrounds an area corresponding to the third patch, (vii) determine a location where similarity between the third patch and a fourth patch is highest as a location of the fourth patch while in the second search area, moving the fourth patch corresponding to the third patch, and (viii) determine the second motion vector based on a location of the third patch and the location of the fourth patch.

3. An apparatus for computed tomography (CT) data reconstruction based on motion compensation, the apparatus comprising:

a storage configured to store N CT projection radiographs, wherein N is a total number of the stored CT projection radiographs, which is equal to or greater than 2; and an image processor configured to obtain pairs of opposite projection radiographs from the N CT projection radiographs, and to determine whether or not a radiography subject has moved based on a correlation between the projection radiographs of each pair of opposite projection radiographs, wherein each of the N/2 pairs of opposite projection radiographs includes a first projection radiograph and a second projection radiograph, and for each of the N/2 pairs of opposite projection radiographs, the image processor is further configured to determine both a first motion vector for the second projection radiograph based on the first projection radiograph and a second motion vector for the first projection radiograph based on the second projection radiograph, wherein the image processor is further configured to perform smoothing filtering on determined N/2 first motion vectors, and to perform the smoothing filtering on determined N/2 second motion vectors, and wherein for each of the N/2 pairs of opposite projection radiographs, the image processor is further configured to (i) perform the motion compensation on the second projection radiograph using the first motion vector so as to generate motion-compensated second projection radiographs, (ii) reconstruct a first sectional image from the motion-compensated second projection radiograph and remaining CT projection radiographs except for second projection radiographs of the N CT projection radiographs, (iii) perform the motion compensation on the first projection radiograph using the second motion vector so as to generate motion-compensated first projection radiographs, (iv) reconstruct a second sectional image using the motion-compensated first projection radiographs and remaining CT projection radiographs except for first projection radiographs of the N CT projection radiographs, (v) identify which image of the first sectional image and the second sectional image has higher resolution, and (vi) determine the motion-compensated second projection radiograph as the motion-compensated projection radiograph when identifying resolution of the first sectional image is higher than resolution of the second sectional image, or determine the motion-compensated first projection radiographs as the motion-compensated projection radiographs when identifying the resolution of the second sectional image is higher than the resolution of the first sectional image.

4. An apparatus for computed tomography (CT) data reconstruction based on motion compensation, the apparatus comprising:

a storage configured to store N CT projection radiographs, wherein N is a total number of the stored CT projection radiographs, which is equal to or greater than 2; and an image processor configured to:

obtain pairs of opposite projection radiographs from the N CT projection radiographs, wherein each pair includes a first projection radiograph and a second projection radiograph;

for each pair, determine whether a radiography subject has moved based on a correlation between the first projection radiograph and the second projection radiograph;

for each pair, when the radiography subject is determined as moved, generate a first motion-compensated projection radiograph using the second projection radiograph, generate a second motion-compensated projection radiograph using the first projection radiograph;

for each pair, select one of the first motion-compensated projection radiograph and the second motion-compensated projection radiograph;

when the first motion-compensated projection radiograph is selected, reconstruct CT data using the first motion-compensated projection radiographs of the N/2 pairs and the second projection radiographs of the N/2 pairs; and when the second motion-compensated projection radiograph is selected, reconstruct CT data using the second motion-compensated projection radiographs of the N/2 pairs and the first projection radiographs of the N/2 pairs.

5. The apparatus of claim 4, wherein the image processor is configured to:

determine a first motion vector for the first projection radiograph based on the second projection radiograph;

determine a second motion vector for the second projection radiograph based on the first projection radiograph;

generate the first motion-compensated projection radiograph by compensating the first projection radiograph using the second motion vector;

generate the second motion-compensated projection radiograph by compensating the second projection radiograph using the first motion vector.

6. The apparatus of claim 4, wherein the image processor is configured to uses one of a patch matching algorithm and a block matching algorithm to determine the first motion vector and the second motion vector.

7. The apparatus of claim 4, wherein the image processor is configured to perform smoothing filtering on N/2 first motion vectors and N/2 second motion vectors for the N projection radiographs.

8. The apparatus of claim 4, wherein the image processor is configured to select one of the first motion-compensated projection radiograph and the second motion-compensated projection radiograph, as an intended motion-compensated radiograph.

9. The apparatus of claim 4, wherein the image processor is configured to:

reconstruct a first CT data using the first motion-compensated projection radiographs and the second projection radiographs for the N/2 pairs of the projection radiographs;

reconstruct a second CT data using the second motion-compensated projection radiographs and the first projection radiographs for the N/2 pairs of the projection radiographs;

select one have a higher resolution than the other between the first CT data and the second CT data;

when the first CT data is selected, select the first motion-compensated projection radiographs for a final CT reconstruction; and otherwise, select the second motion-compensated projection radiographs for the final CT reconstruction.

* * * * *